United States Patent [19]

Voth et al.

[11] Patent Number: Plant 7,172

[45] Date of Patent: Feb. 27, 1990

[54] STRAWBERRY PLANT CALLED IRVINE

[75] Inventors: Victor Voth, Santa Ana; Royce S. Bringhurst, Davis, both of Calif.

[73] Assignee: The Regents of the University of California, Berkeley, Calif.

[21] Appl. No.: 269,928

[22] Filed: Nov. 9, 1988

[51] Int. Cl.[4] ..... A01H 5/00

[52] U.S. Cl. ..... Plt./49

[58] Field of Search ..... Plt./49

*Primary Examiner*—James R. Feyrer

*Attorney, Agent, or Firm*—Townsend and Townsend

[57] ABSTRACT

This invention relates to a new and distinct day-neutral variety of strawberry plant called 'Irvine'. The variety has a chilling requirement lower than 'Selva'. It has a high yield and produces a large, firm fruit which is symmetrical and ranges from conic medium to flat and wedgy in shape. The variety is quite flexible in that it can be planted commercially or in the home garden and the fruit is recommended for the fresh market or for processing. The fruit of 'Irvine' is juicier and has a better flavor than 'Selva'.

2 Drawing Sheets

DESCRIPTION

This invention relates to a new and distinctive day-neutral type strawberry cultivar designated 'Irvine' which is the result of a cross of 'Douglas' (U.S. Plant Pat. No. 4,487)×'Muir' (U.S. Plant Pat. No. 6,558), made in 1982.

'Irvine' first fruited at the University of California South Coast Field Station, Irvine, Calif. in 1983, where it was selected and designated originally as Cal 82:14-603. It was tested later as advanced selection CN 14.

'Irvine' has been propagated asexually by runners and has been tested at various University of California field stations and research facilities and to a limited extent in growers' fields under Test Agreement.

In the photographs:

Figure 1:
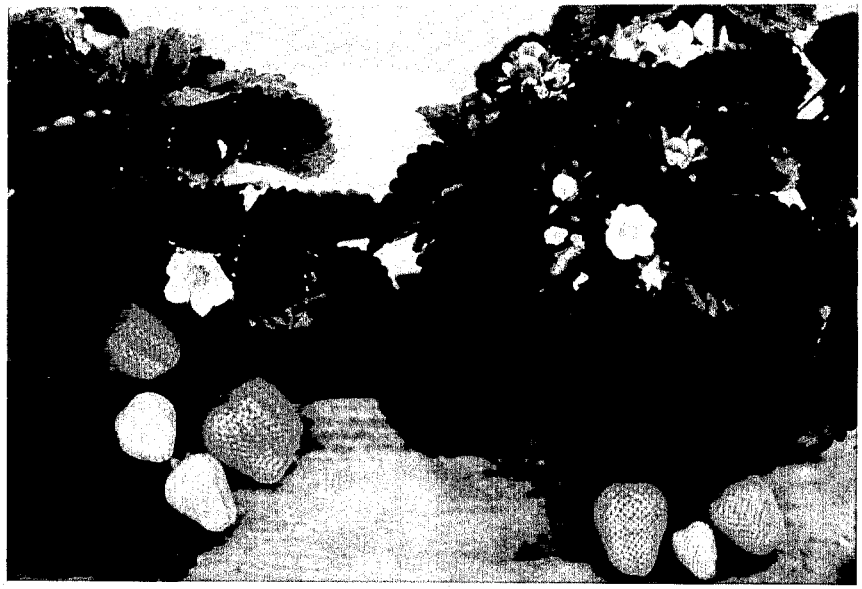
FIG. 1 shows typical early season growth, flowering and fruiting characteristics of the plant.
Figure 2:
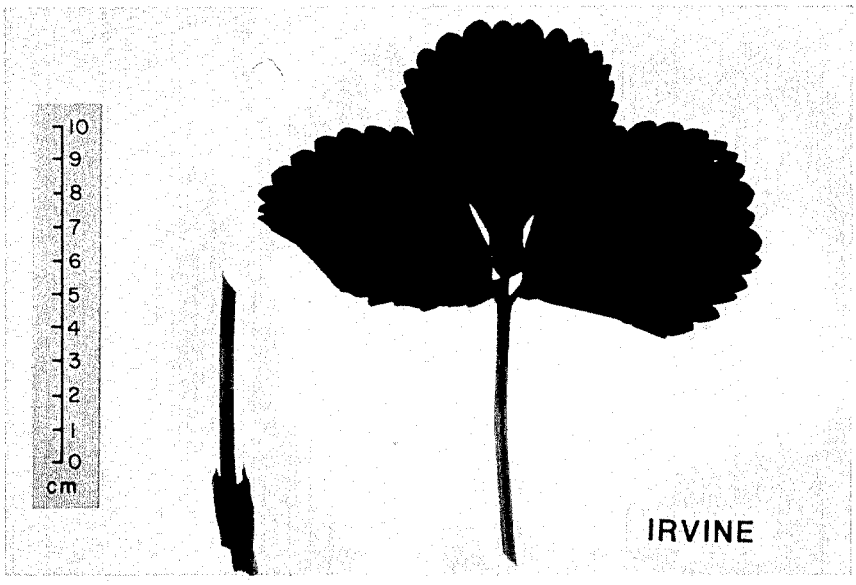
FIG. 2 shows a typical early-season mature leaf from a fruiting plant.
Figure 3:
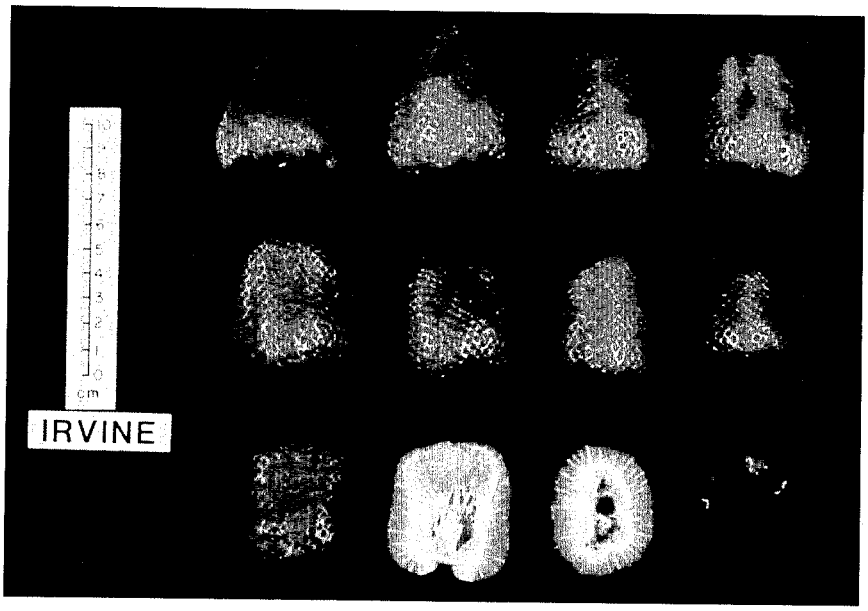
FIG. 3 shows individual representative early-season fruit with longitudinal and cross-sectional views.

'Irvine' commences fruiting about three months after planting, whether freshly dug or cold storage plants are used, and regardless of planting time provided that satisfactory growing conditions prevail. 'Irvine' is a stronger day-neutral than 'Selva' (U.S. Plant Pat. No. 5,266), or 'Muir' but not quite as strong as 'Hecker' (U.S. Plant Pat. No. 4,507) or 'Fern' (U.S. Plant Pat. No. 3,267). The difference is most evident in the nursery where only the mother and first daughter plants of 'Selva' and to a somewhat greater extent 'Muir' tend to flower and fruit strongly, whereas most of the daughter plants of 'Hecker' and 'Fern' and to a somewhat lesser extent 'Irvine' do so. Thus, ranking them in order of the tendency for plants to flower in the nursery in order would be: 'Hecker'—'Fern'—'Irvine'—'Muir'—'Selva'. All are heterozygous for the day-neutral trait.

'Irvine' is of particular interest for winter plantings in situation where 'Selva' is used successfully.

Plants and foliage: Fruiting 'Irvine' plants are more erect in growth habits than those of 'Muir' and much more so than those of 'Selva'. Leaf characteristics from mid-summer 1988 central coast grown fruiting plants of 'Irvine' are compared with those of 'Muir', 'Selva', 'Fern' and 'Douglas' in Table 1:

TABLE 1

| | IRVINE | MUIR | SELVA | FERN | DOUGLAS |
|---|---|---|---|---|---|
| Munsell Color | 7.5GY4/4 | 2.5GY4/3 | 7.5GY4/4 | 7.5GY4/4 | 2.5G/Y6/8 |
| Shape (length/width) | 1.10 | 1.02 | 1.10 | 1.14 | 1.09 |
| Base angle of terminal leaflet | 53 | 60 | 55 | 50 | 49 |
| Size of terminal leaflets | 76 | 84 | 81 | 76 | 87 |
| Serrations of terminal leaflet | 9.4 | 11.2 | 11.2 | 12.0 | 10.6 |
| Petiolule length (MM) | 6.6 | 6.6 | 10.4 | 6.4 | 11.8 |
| Petiole length (MM) | 150 | 137 | 152 | 154 | 191 |

As shown above 'Irvine' leaves are about the same color as those of 'Selva' and 'Fern' but lighter and more yellow than those of 'Muir' or 'Douglas' (Munsell Color System—Nickerson Color Fan). Terminal leaflets are somewhat similar in shape to those of 'Selva' or 'Douglas' but less round than those of 'Muir' as shown by the length/width measurement and half/blade terminal leaflet basal angle. 'Irvine' terminal leaflets are about the same size as those of 'Fern', smaller than those of 'Muir', 'Selva' and 'Douglas' as determined by extracting the square root of the length×width measurements. Terminal leaflet serration numbers are less than those for all the comparison cultivars. The length of the terminal leaflet petiolules of 'Irvine' is about the same as those of 'Muir' or 'Fern' but considerably shorter than those of 'Selva' and 'Douglas'. 'Irvine' plants are about the same size as those of 'Selva' or 'Fern', larger than those of 'Muir' but much smaller than those of 'Douglas' as indicated by petiole length. Bract leaflets are rare on 'Irvine' petioles in contrast to 'Muir' and 'Selva'. Runner production in nursery plants of 'Irvine' is very good, about equal to or better than for 'Selva' and 'Muir'.

Isozymes in leaf extracts: 'Irvine' has been classified for three enzyme systems by starch gel electrophoresis: A. Phosphoglucoisomerase (PGI); B. Leucine amino peptidase (LAP) and C. Phosphoglucomutase (PGM); and the results are compared with those for the other day-neutral California cultivars in Table 2.

TABLE 2

| | IRVINE | MUIR | SELVA | FERN |
|---|---|---|---|---|
| PGI | A3 | A2 | A2 | A4 |
| LAP | B1 | B1 | B3 | B3 |
| GM | C1 | C2 | C2 | C2 |

| | HECKER | APTOS & BRIGHTON | MRAK | YOLO |
|---|---|---|---|---|
| PGI | A1 | A4 | A1 | A1 |
| LAP | B1 | B3 | B3 | B1 |
| GM | C4 | C4 | C2 | C2 |

Thus, 'Irvine' with the pattern A3 (heterozygous for the fast band), B1 and C1 can be distinguished from all other U.C. day-neutrals unambiguously with these three systems. 'Irvine' can also be distinguished unambiguously from the presently important California standard type cultivars including: 'Chandler', 'Douglas', 'Pajaro', 'Parker' and 'Oso Grande'. For the procedure see: J. Amer. Soc. Hort. Sci. 106:684–687, 1981).

Disease and pest reaction: 'Irvine' is highly resistant to (tolerant of) the virus diseases common in California including 'Mild Yellow Edge' and complexes containing it, probably quite susceptible to Verticillum wilt, (since both parents are), moderately susceptible to the two-spotted mite.

Flowering, fruiting, fruit and production characteristics: 'Irvine' is similar to California day-neutral cultivars 'Selva' and 'Muir' in that with a minimum of conditioning, it will flower and fruit anytime, effectively independent of day length. Flowers are borne on long, relatively thick peduncles, even more erect than those of 'Muir' and much more erect than those of 'Selva' and they tend to remain so until the weight of the fruit brings them down. The flowers have large attractive petals (5 to 8 averaging about 6). 'Irvine' is self-fertile providing ample pollen through-out the season and pollination is generally good as relatively few malformed fruit form.

'Irvine' is capable of yielding about as much as other high yielding day-neutral and short-day type cultivars and the fruit size is almost as large on the average as that of 'Selva' and 'Muir' (Tables 3 and 4). 'Irvine' has a lower chilling requirement than 'Selva' and can probably be planted earlier than 'Selva' with favorable results (Tables 3 and 4). Size varies considerably on 'Irvine' as the season advances or environmental conditions change.

'Irvine' fruit shape is characteristically medium conic, but sometimes flat or wedgy; centers may be hollow. 'Irvine' fruit quality characteristics (soluble solids, firmness, ascorbic acid and color) are compared with those of 'Selva', 'Muir', 'Chandler', 'Douglas', 'Pajaro' and 'Oso Grande' from plants grown under optimum conditions under the "hill" system in winter plantings at the University of Califor1ia Strawberry Research Facility, Watsonville in Table 5.

TABLE 3

Comparing 1987 yield and fruit size of high elevation (MacDoel) plants of 'Irvine' with that of standard cultivars and 'Selva' dug Oct. 15 and winter planted at the South Coast Field Station, Irvine.

| CULTIVAR | G/PL BY PERIODS ENDING: 2/28 | 3/31 | 4/30 | 5/31 | 6/30 | TOTAL YLD G/PL | S.D. | SIZE G/FR |
|---|---|---|---|---|---|---|---|---|
| IRVINE | 61 | 181 | 674 | 230 | 291 | 1441 | 72 | 20.6 |
| SELVA | 91 | 133 | 319 | 171 | 217 | 935 | 75 | 17.0 |
| CHANDLER | 74 | 45 | 805 | 442 | 258 | 1627 | 45 | 20.8 |
| OSO GRANDE | 70 | 36 | 878 | 330 | 165 | 1482 | 81 | 25.6 |
| PARKER | 110 | 88 | 681 | 262 | 253 | 1398 | 79 | 23.5 |
| DOUGLAS | 77 | 59 | 706 | 267 | 282 | 1395 | 55 | 22.5 |

TABLE 4

Comparing 1987 yield and fruit size of high elevation (MacDoel) plants of 'Irvine' with that of 'Muir' and 'Selva' dug Oct. 15 and planted as indicated at the U.C.D. Strawberry Research Facility, Watsonville.

| CULTIVAR | PLTD | G/PL BY PERIODS ENDING: 4/20 | 6/4 | 7/13 | 8/24 | 10/5 |
|---|---|---|---|---|---|---|
| IRVINE | 11/4 | 179 | 803 | 432 | 380 | 207 |
| | 11/19 | 111 | 757 | 616 | 470 | 217 |
| MUIR | 11/4 | 245 | 753 | 309 | 429 | 197 |
| | 11/19 | 126 | 884 | 460 | 469 | 218 |
| SELVA | 11/4 | 240 | 449 | 235 | 445 | 158 |
| | 11/19 | 227 | 727 | 361 | 527 | 161 |

| CULTIVAR | PLTD | TOTAL YLD G/PL | S.D. | SIZE G/FR |
|---|---|---|---|---|
| IRVINE | 11/4 | 2007 | 308 | 19.5 |
| | 11/19 | 2174 | 172 | 20.9 |
| MUIR | 11/4 | 1935 | 5 | 19.1 |
| | 11/19 | 2159 | 173 | 20.3 |
| SELVA | 11/4 | 1529 | 76 | 19.8 |
| | 11/19 | 2005 | 37 | 21.5 |

According to our measurements, 'Irvine' fruit was comparable to those of 'Douglas', 'Oso Grande' and 'Pajaro' in soluble solids, perhaps a little less than those 'Muir', 'Selva' or 'Chandler'. The fruit of 'Irvine' is very firm, about equal to 'Selva' and 'Oso Grande' as measured by a pentetrometer equipped with a 'Hunter Force Gage' and it stores and ships about as well as 'Selva'. However, 'Irvine' fruit appears to be quite sensitive to rain damage.

TABLE 5

Comparing fruit quality characteristics of 'Irvine' with those for standard short-day and day-neutral types of mid-summer fruit from the U.C.D. Strawberry Research Facility, Watsonville.

| CULTIVAR | SOLIDS % | SIGNIF. | FIRMNESS PENET. | S.D. | ASCORBIC MG/100 | S.D. | MUNSELL COLOR |
|---|---|---|---|---|---|---|---|
| MUIR | 8.6 | a | 7.0 | 0.5 | 26.9 | 1.7 | 7R4.5/13 |
| SELVA | 8.5 | ab | 7.7 | 0.2 | 26.9 | 2.7 | 7R4/11 |
| CHANDLER | 8.3 | ab | 6.2 | 0.4 | 29.8 | 4.6 | 5R4/12 |
| DOUGLAS | 8.1 | abc | 5.2 | 0.4 | 31.7 | 5.5 | 6R4/12 |
| OSO | 7.7 | abc | 7.7 | 0.4 | 32.4 | 3.1 | 7.5R4.5/11 |
| IRVINE | 7.1 | c | 7.8 | 0.4 | 26.2 | 6.7 | 7R5/14 |
| PAJARO | 7.0 | c | 7.3 | 0.2 | 36.2 | 1.4 | 5R4/12 |

'Irvine' fruit averaged about as high in ascorbic acid content as 'Selva' or 'Muir' but less than 'Chandler', 'Douglas', 'Oso' and 'Pajaro' as measured by the Loeffler and Ponting method (1942, J. Indust. and Engin. Chem. 14:846).

The fruit skin color is less red than that of 'Selva' but much less red than that of 'Chandler', 'Pajara' or 'Douglas' (ibid.). The finish is particularly bright and attractive. The flesh is about the same as the skin but less intense with a slightly lighter ring around the core. The achenes are bright yellow to slightly reddish, positioned about flush with the skin surface. The calyx is medium to large sized, positioned from even with the base of the fruit to being borne on a short rather thick neck, somewahat reflexed.

The flavor of 'Irvine' fruit is as good or better than that of 'Selva' and is slightly more juicy. The fruit is recommended for fresh market and processing, for commercial planting and home gardening, particularly where "off season" fruiting is desirable. The only cultivars that 'Irvine' resembles closely in performance are 'Selva' and 'Muir' and consequently it is of interest wherever 'Selva' is currently grown.

We claim:

1. The new and distinct variety of strawberry plant herein described and illustrated and identified by the characteristics enumerated above.

* * * * *

UNITED STATES PATENT AND TRADEMARK OFFICE

CERTIFICATE OF CORRECTION

PATENT NO. : Plant 7,172

DATED : February 27, 1990

INVENTOR(S) : Bringhurst, et al.

It is certified that error appears in the above-identified patent and that said Letters Patent is hereby corrected as shown below:

Column 3, line 12, in the subcolumn corresponding to the cultivar IRVINE, delete "B1" and substitute --B3--.

Signed and Sealed this

Sixth Day of October, 1992

*Attest:*

*Attesting Officer*

DOUGLAS B. COMER

*Acting Commissioner of Patents and Trademarks*